United States Patent
Quada, Jr. et al.

(10) Patent No.: US 6,720,349 B2
(45) Date of Patent: Apr. 13, 2004

(54) COMPOUNDS FOR USE IN THE TREATMENT OF CANCER OR VIRAL INFECTIONS

(75) Inventors: James C. Quada, Jr., San Antonio, TX (US); Joseph K. Agyin, San Antonio, TX (US); James Berger Camden, West Chester, OH (US)

(73) Assignee: UAF Technologies and Research, LLC, Tucson, AZ (US)

( * ) Notice: Subject to any disclaimer, the term of this patent is extended or adjusted under 35 U.S.C. 154(b) by 50 days.

(21) Appl. No.: 10/132,545

(22) Filed: Apr. 25, 2002

(65) Prior Publication Data

US 2002/0193609 A1 Dec. 19, 2002

Related U.S. Application Data

(62) Division of application No. 09/670,170, filed on Sep. 26, 2000, now Pat. No. 6,380,232.

(51) Int. Cl.⁷ ................... A61K 31/4184; C07D 235/30
(52) U.S. Cl. ..................................... 514/388; 548/308.7
(58) Field of Search ........................ 548/308.7; 514/388

(56) References Cited

U.S. PATENT DOCUMENTS

| | | | |
|---|---|---|---|
| 2,933,502 A | | 4/1960 | Klopping |
| 3,010,968 A | | 11/1961 | Loux |
| 3,370,957 A | | 2/1968 | Wagner et al. |
| 3,399,212 A | | 8/1968 | Hoover et al. |
| 3,480,642 A | | 11/1969 | Stedman et al. |
| 3,499,761 A | | 3/1970 | Dersch et al. |
| 3,541,213 A | | 11/1970 | Klopping |
| 3,669,969 A | | 6/1972 | Lunn |
| 3,738,995 A | | 6/1973 | Adams et al. |
| RE28,403 E | * | 4/1975 | Actor et al. ............. 260/309.2 |
| 3,881,014 A | | 4/1975 | Regel et al. |
| 3,933,846 A | * | 1/1976 | Daum ..................... 260/309.2 |
| 3,956,262 A | | 5/1976 | Heyes et al. |
| 4,001,423 A | * | 1/1977 | Dodds ........................ 424/273 |
| 4,046,906 A | | 9/1977 | Frensch et al. |
| 4,053,598 A | | 10/1977 | Daum et al. |
| 4,086,235 A | | 4/1978 | Beard |
| 4,731,366 A | | 3/1988 | Munro et al. |
| 4,814,329 A | | 3/1989 | Harsanyi et al. |
| 5,098,923 A | | 3/1992 | Karjalainen et al. |
| 5,114,951 A | | 5/1992 | King |
| 5,149,527 A | | 9/1992 | Weisenthal |
| 5,284,662 A | | 2/1994 | Koparkar et al. |
| 5,290,801 A | | 3/1994 | Higley et al. |
| 5,310,748 A | | 5/1994 | Wilde et al. |
| 5,329,012 A | | 7/1994 | Anderson |
| 5,364,875 A | | 11/1994 | Wilde |
| 5,434,163 A | | 7/1995 | Edlind et al. |
| 5,441,742 A | | 8/1995 | Autant et al. |
| 5,554,373 A | | 9/1996 | Seabrook et al. |
| 5,629,341 A | | 5/1997 | Camden |
| 5,656,615 A | | 8/1997 | Camden |
| 5,665,713 A | | 9/1997 | Camden |
| 5,665,751 A | | 9/1997 | Camden |
| 5,767,138 A | | 6/1998 | Camden |
| 5,770,616 A | | 6/1998 | Camden |

(List continued on next page.)

FOREIGN PATENT DOCUMENTS

| | | | |
|---|---|---|---|
| BE | 667158 | | 11/1965 |
| DE | 2144505 A1 | * | 3/1973 |
| EP | 0617968 A1 | | 10/1994 |
| FR | 2046114 | * | 3/1971 |
| FR | 2155888 | | 10/1973 |
| GB | 1123317 | | 8/1968 |
| GB | 1296561 | | 11/1972 |
| GB | 1397886 | | 6/1975 |
| IN | 158878 A | | 2/1987 |
| IN | 159210 A | | 4/1987 |
| JP | 51/034161 A2 | * | 3/1976 |
| JP | 07277956 | | 10/1995 |
| WO | WO 94/04541 | | 3/1994 |
| WO | WO 96/32103 | | 10/1996 |
| WO | WO 96/32104 | | 10/1996 |
| WO | WO 96/32107 | | 10/1996 |
| WO | WO 96/32115 | | 10/1996 |
| WO | WO 96/40119 | | 12/1996 |
| WO | WO 96/40120 | | 12/1996 |
| WO | WO 96/40122 | | 12/1996 |
| WO | WO 97/05870 | | 2/1997 |
| WO | WO 97/05872 | | 2/1997 |
| WO | WO 97/05873 | | 2/1997 |
| WO | WO 98/32440 | | 7/1998 |

(List continued on next page.)

OTHER PUBLICATIONS

Schroeder et al., CA 78:159686, 1973.*

Sawatari et al., CA 84:164780, 1976.*

Suenobu et al., CA 85:108639, 1976.*

CA Registry No. 83601–82–5, 1982.*

Khasanov et al., CA 95:24913, 1981.*

Bekish et al., CA 92:34059, 1980.*

CA 75:151800, 1971.*

Daum, CA 80:82979, 1974.*

Actor et al. CA 84:4950, 1976.*

An English Translation of FR 2,046,114, 1971.*

(List continued on next page.)

*Primary Examiner*—Laura L. Stockton
(74) *Attorney, Agent, or Firm*—Haynes and Boone, LLP

(57) ABSTRACT

Benzimidazole derivatives and salts and prodrugs thereof are disclosed, together with methods for the treatment of cancers or viral infections in warm blooded animals by administration of these compounds. Such compounds may be used in combination with a chemotherapeutic agent and/or a potentiator.

16 Claims, No Drawings

U.S. PATENT DOCUMENTS

| | | | |
|---|---|---|---|
| 5,840,742 | A | 11/1998 | Camden |
| 5,854,231 | A | 12/1998 | Camden |
| 5,872,142 | A | 2/1999 | Camden |
| 5,880,144 | A | 3/1999 | Camden |
| 5,900,429 | A | 5/1999 | Camden |
| 5,902,804 | A | 5/1999 | Camden |
| 5,908,855 | A | 6/1999 | Camden |
| 5,929,099 | A | 7/1999 | Camden |
| 5,932,604 | A | 8/1999 | Camden |
| 5,932,609 | A | 8/1999 | Camden |
| 5,958,950 | A | 9/1999 | Padia et al. |
| 6,025,377 | A | 2/2000 | Camden |
| 6,077,862 | A | 6/2000 | Camden |
| 6,090,796 | A | 7/2000 | Camden |
| 6,110,953 | A | 8/2000 | Camden |
| 6,136,835 | A | 10/2000 | Camden |
| RE37,003 | E | 12/2000 | Camden |
| 6,177,460 | B1 | 1/2001 | Camden |
| 6,200,992 | B1 | 3/2001 | Camden |
| 6,211,177 | B1 | 4/2001 | Sperl et al. |
| 6,228,876 | B1 | 5/2001 | Camden |
| 6,245,789 | B1 | 6/2001 | Camden |
| 6,251,870 | B1 | 6/2001 | Camden |
| 6,262,093 | B1 | 7/2001 | Camden |
| 6,265,427 | B1 | 7/2001 | Camden |
| 6,271,217 | B1 | 8/2001 | Camden |
| 6,290,929 | B1 | 9/2001 | Camden |
| 6,329,355 | B1 | 12/2001 | Camden |
| 6,362,207 | B1 | 3/2002 | Camden |
| 6,380,232 | B1 | 4/2002 | Quada, Jr. et al. |
| 6,384,049 | B1 | 5/2002 | Camden |
| 6,407,105 | B1 | 6/2002 | Quada, Jr. et al. |
| 6,407,131 | B1 | 6/2002 | Quada, Jr. et al. |
| 2001/0002403 | A1 | 5/2001 | Camden |
| 2001/0027205 | A1 | 10/2001 | Camden |
| 2001/0039291 | A1 | 11/2001 | Camden |
| 2001/0041678 | A1 | 11/2001 | Camden |
| 2001/0047015 | A1 | 11/2001 | Camden |
| 2001/0053773 | A1 | 12/2001 | Camden |
| 2002/0019415 | A1 | 2/2002 | Camden |

FOREIGN PATENT DOCUMENTS

| | | |
|---|---|---|
| WO | WO 98/51303 | 11/1998 |
| WO | WO 98/51304 | 11/1998 |
| WO | WO 99/59585 | 11/1999 |
| WO | WO 00/21504 | 4/2000 |
| WO | WO 00/50007 | 8/2000 |
| WO | WO 01/12169 A2 | 2/2001 |
| WO | WO 01/83457 A2 | 11/2001 |
| WO | WO 01/89499 A2 | 11/2001 |
| WO | WO 02/09715 A2 | 2/2002 |
| WO | WO 02/09716 A2 | 2/2002 |
| WO | WO 02/26716 A2 | 4/2002 |
| WO | WO 02/41891 A2 | 5/2002 |

OTHER PUBLICATIONS

Pending Application of Camden, Ser. No. 09/360,499, filed Jul. 26, 1999. (578 1D).

Pending Application of Camden, Ser. No. 09/371,457, filed Aug. 10, 1999. (5784R).

Pending Application of Camden, Ser. No. 09/371,459, filed Aug. 10, 1999. (5784R2).

Pending Application of Camden, Ser. No. 09/312,948, filed May 17, 1999. (5786D).

Pending Application of Camden, Ser. No. 09/394,383, filed Sep. 10, 1999. (5786DR).

Pending Application of Camden, Ser. No. 08/857,811, filed May 16, 1997, CPA filed Jul. 28, 1999. (6643).

Pending Application of Camden, Ser. No. 09/374,717, filed Aug. 13, 1999. (7719).

Pending Application of Camden, Ser. No. 09/462,243, filed Jan. 5, 2000. (6642).

Pending Application of Camden, Ser. No. 09/552,825, filed Apr. 20, 2000. (6643D2).

Pending Application of Camden, Ser. No. 09/552,820, filed Apr. 20, 2000. (6643D3).

Pending Application of Camden, Ser. No. 09/560,059, filed Apr. 27, 2000 (5781D3).

Pending Application of Camden, Ser. No. 09/603,040, filed Jun. 26, 2000. (5781DC).

Pending Application of Camden, Ser. No. 09/791,986, filed Apr. 28, 2000. (8068).

Pending Application of Camden, Ser. No. 09/562,709, filed Apr. 28, 2000. (8069).

Pending Application of Camden, Ser. No. 09/602,170, filed Jun. 22, 2000. (5783C2).

Pending Application of Camden, Ser. No. 09/603,322, filed Jun. 26, 2000. (5781D2).

Pending Application of Camden, Ser. No. 09/618,990, filed Jul. 18, 2000. (5702CRD).

Pending Application of Camden, Ser. No. 09/639,188, filed Aug. 15, 2000. (5784R2D).

Pending Application of Camden, Ser. No. 09/640,148, filed Aug. 16, 2000. (5784R2C).

Pending Application of Camden, Ser. No. 09/645,708, filed Aug. 24, 2000. (5785D2RD).

Pending Application of Camden, Ser. No. 09/645,427, filed Aug. 24, 2000. (5785D2RD2).

Pending Application of Camden, Ser. No. 09/640,920, filed Aug. 17, 2000. (7161R2).

Pending Application of Camden, Ser. No. 09/640,918, filed Aug. 17, 2000. (7161R3).

Pending Application of Camden, Ser. No. 09/640,919, filed Aug. 17, 2000. (7161R4).

Pending Application of Camden, Ser. No. 09/676,407, Sep. 29, 2000. (6643R).

Pending Application of Camden, Ser. No. 09/676,034, filed Sep. 29, 2000. (6643R2).

Pending Application of Camden, Ser. No. 09/676,033, filed Sep. 29, 2000. (6643R3).

Pending Application of Camden, Ser. No. 09/676,409, filed Sep. 29, 2000. (6643R4).

Pending Application of Camden, Ser. No. 09/676,032, filed Sep. 29, 2000. (6643R5).

Pending Application of Camden, Ser. No. 09/676,031, filed Sep. 29, 2000. (6643R6).

Pending Application of Camden, Ser. No. 09/676,029, filed Sep. 29, 2000. (6643R8).

Pending Application of Camden, Ser. No. 09/676,408, filed Sep. 29, 2000. (6643R9).

Pending Application of Camden, Ser. No. 09/676,202, filed Sep. 29, 2000. (6643R10).

Pending Application of Camden, Ser. No. 09/670,168, filed Sep. 26, 2000. (8251).

Pending Application of Camden, Ser. No. 09/670,166, filed Sep. 26, 2000. (8253).

Pending Application of Camden, Ser. No. 09/703,955, filed Nov. 1, 2000. (8315).

Pending Application of Camden, Ser. No. 10/106,429, filed Mar. 26, 2002. (5638D2CDC).

Agarwal, et al., "Antiparasitic agents. Part XVI. Synthesis of 5(6)–substituted benzimidazole–2–carbamates as anthelmintic agents", Indian J. Chem., Sect. B, 32B(4), pp. 453–456, (1993), American Chemical Society (Abstract only).

Agarwal, et al., "Segregation of activity profile in benzimidazoles: Effect of spacers at 5(6)–position of methyl benzimidazole–2–carbamates", Z. Naturforsch., C; Biosci., 48(11–12), pp. 829–838, (1993), American Chemical Society (Abstract only).

Agrawal, et al. "Synthesis of 2–substituted 5(6)–aroylaminobenzimidazoles as potential anthelmintics", Indian J. Chem., Sect. B, 22B(2), pp. 146–149, (1983), American Chemical Society (Abstract only).

Atassi, et al., "R17934–NSC 238159: A New Antitumor Drug", Europ. J. Cancer, vol. 11, pp. 599–607, (1975), Pergamon Press.

Aur, "Treatment of Parasitic Infestation in Children with Malignant Neoplams", The Journal of Pediatrics, vol. 78, No. 1, pp. 129-131, (1971), Mosby, Inc.

Beard, "5 (6)–Benzeme ring–substituted benzimidazole–2–carbamate derivative having anthelmintic activity", U.S. patent 4,086,235 A, (1978), American Chemical Society (Abstract Only).

Berg et al., "Synergistic effects of photoactivated tetra(4–sulfonatophenyl)porphine and nocodazole on microtubule assembly, accumulation of cells in mitosis and cell survival.", Journal of Photochemistry and Photobiology B: Biology, vol. 13, pp. 59–70, (1992), Elsevier Sequoia.

Berg et al., "Synergistic effects of photoactivated tetra(4–sulfonatophenyl)porphine and nocodazole on microtubule assembly, accumulation of cells in mitosis and cell survival.", Journal of Photochemistry and Photobiology B: Biology, vol. 13, pp. 59–70, (1992), American Chemical Society, (Abstract only).

Bissery, et al., "Preclinical Profile of Docetaxel (Taxotere): Efficacy as a Single Agent and in Combination", Seminars in Oncology, vol. 22, No. 6–S13, pp. 3–16, (1995), W.B. Saunders Company.

Brabender, et al., "The Effects of Methyl [5–(2–Thienylcarbonyl)–1H–benzimidazol–2–yl]carbamate, (R 17934; NSC 238159), a New Antitumoral Drug Interfering with Microtubules", Cancer Research, vol. 36, pp. 905–916, (1976), American Association of Cancer Research.

Brown, et al., "Antiparasitic Drugs. IV. 2–(4'–Thiazolyl)–Benzimidazole, A New Anthelmintic", Journal of American Chemical Society, pp. 1764–1765, (1961), American Chemical Society.

Carter et al., "Drug–Tumor Interactions", Chemotherapy of Cancer, $2^{nd}$ Ed., pp. 362–365, (1981), John Wiley & Sons.

Carter, "2–(α–Hydroxybenzyl)–Benzimidazole", Selective Inhibitors of Viral Functions, pp. 277–346, (1975), CRC Press, Inc.

Canicio Chimeno, Process for the perparation of alkyl N'–alkylcarbamoyl–N–(2–benimidazolyl) carbamates, (1987), Chemical Abstracts 107:39817, American Chemical Society.

"Daum et al., 2,4–Dioxo–1, 2, 3, 4–tetrahydro–s–triazino [1,2–a] benzimidazoles", Chemical Abstract 86:155704, (1977), American Chemical Society.

Delatour, et al., "Embryotoxic and Antimitotic Properties in the Benzimidazole Series", pp. 505–515, (1976), Therapie, vol. 31, No. 4, John Libbey & Co., Ltd., (English translation thereof).

"Divakar, et al., Synthesis and antifilarial activity of benzimidazole–2–carbamates carrying an amino acid side chain at the 5(6)–position", Indian J. Chem., Sect. (B), 28B(3), pp. 252–260, (1989), American Chemical Society (Abstract only).

"Dubey, et al., Synthesis and anthelmintic activity of 5(6)–[benzimidazole–2–yl)carboxamido]–and (4–substituted piperazin–l–y) benzimidazoles", J. Med. Chem., 28(11), pp. 1748–1750, (1985), American Chemical Society (Abstract only).

"Dubey, et al., Synthesis of 4–(aryl/arylcarbonyl)amino– and 4–arylthio/arysulfonyl–7–chloroquinolines as potential antiparasitic agents", Indian J. Chem., Sect. B, 24B(4), pp. 408–413, (1985), American Chemical Society (Abstract only).

Elgebaly, et al., "Reversal of gamma–Radiation–Induced Leukemogenesis in Mice by Immunomodulation with Thiabendazole and Dinitrofluorobenzene", pp. 811–815 (1985), Chemical Abstracts 102:217569, American Chemical Society.

Elgebaly, et al., "Reversal of gamma–Radiation–Induced Leukemogenesis in Mice by Immunomodulation with Thiabendazole and Dinitrofluorobenzene", J. Natl. Cancer Inst., pp. 811–815 (1985), Oxford University Press.

Friedman, et al., "Interaction of Anthelmintic and Benzimidazole Derivaives with Bovine Brain Tubulin", Biochimica et Biophysica Acta, pp. 605–614, (1978), Elsevier/North–Holland Biomedical Press.

Gao, et al., "Antihydatidosis drugs: synthesis of benzimidazoles", Zhongguo Yiyao Gongye Zazhi, 20(3), pp. 110–115, (1989), American Chemical Society (Abstract only).

Georgopapadakou, et al., "Human Mycoses: Drugs and Targets for Emerging Pathogens", Science, vol. 264, pp. 371–373, (1994), American Association for the Advancement of Science.

Ghannoum, et al., "Combinations of antifungal and antineoplastic drugs with interactive effects on inhibition of yeast growth", Chemotherapy, pp. 308–320, (1990), American Chemical Society (Abstract only).

Graubaum, et al., "Acylation of Heterocycles with Carbonic Acid Derivatives", J. Prakt. Chem., pp. 809–815, (1982), American Chemical Society (Abstract only).

Grenda, et al., "Novel Preparation of Benzimidazles from N–Arylamidines. New Synthesis of Thiabendazole", Journal Organic Chemistry, vol., 30, pp. 259–261, (1965), Academic Press.

Hoover et al., Benzimidazolyl Ureas, Chemical Abstract 70:11697, (1969), American Chemical Society.

Katiyar, et al., "Antiprotozoal activities of benzimidazoles and correlations with beta–tubulin sequence", Chemical Abstracts 121:175012z, (1994), American Chemical Society.

Kumar, et al., "Antiparasitic agents. Part XI. Synthesis and anthelmintic activity of 1–substituted 6–18–[2–carbomethoxyamino)benzimidazole]–5–carbonylamino–9H–pyrido[3,4–b] indoles", Indian J. Chem., Sect. B, 29B(11), pp. 1077–1080, (1990), American Chemical Society, (abstract only).

Kumar, et al., "Syntheses and anthelmintic activity of alkyl 5(6)–(substituted carbamoyl)– and 5(6)–(disubstituted carbamoyl)benzimidazole–2–carbamates and related compounds", J. Med. Chem., 27(8), pp. 1083–1089, (1984), American Chemical Society (Abstract only).

Lacey, et al., "Activity of Benzimidazole Carbamates against L1210 Mouse Leukemia Cells Correlation with in vtiro Tubulin Polymerization Assay", Biochemical Pharmacology, vol. 34, No. 19, pp. 3603–3605, (1985), Pergamon Press Ltd.

Lacey, et al., "Structure–Activity Relationships of Benzimidazole Carbmates as Inhibitors of Mammalian Tubulin, in vitro", Biochemical Pharmacology, Vol 34, No. 7, pp. 1073–1077, (1985), Pregamon Press Ltd.

Lacey, et al., "The Role of the Cytoskeletal Protein, Tubulin, in the Mode of Action and Mechanism or Drug Resisteance to Benzimidazoles", International Journal of Parasitology, vol. 18, No. 7, pp. 885–936, (1988), Pergamon Press Ltd.

Lapras, et al. "Experimental Study of the Potential Anticancerous Properties of Parbendazole (SKF 29044)", pp. 379–397, (1975), Bull. Soc. Vet. et Med. comparee, Lyon, vol. 77, No. 6, Societe des Sciences veterinaries et de Medecine comparee de Lyon, (in French and English translation thereof.).

Latif et al., "Relationship between the anthelmintic activity of eight derivatives of benzimidazole carbamates against *Trichinella spiralis* and their chemical structures," Jpn. J. Med. Sci. Biol., 46(5–6), pp. 203–214, (1993), American Chemical Society (Abstract Only).

Lessnau, et al., "Disseminated Strongyloides stercoralis in Human Immunodeficiency Virus–infected Patients", Chest, vol. 104, pp. 119–122, (1993), American College of Chest Physicians.

Lovett, "Immunomodulating Effects of Thiabendazole: Immunotherapeutic Efficacy in the Treatment of Murine Fibrosarcoma", Dissertation Abstracts International, Health Science, Immunology, vol. 39, No. 11, pp. 5315–5316, (1979), U M I.

Lundy, et al., "Chemoimmunotherapy of a murine fibrosarcoma: critical factors for success of combined modality therapy", J. Surg. Oncol., pp. 339–345, (1977), American Chemical Society. (Abstract Only).

Lundy, et al., "Immunomodulation with Thiabendazole: A Review of Immunologic Properties and Efficacy in Combined Modality Cancer Therapy", Cancer Treatments Reports, vol. 62, No. 11, pp. 1955–1962, (1978), U.S. Department of Health, Education, and Welfare.

Lundy, et al., "Thiabendazole: A New Immunopotentiator Effective in Therapy of Murine Fibrosarcoma", Surgical Forum, vol. 27, No. 62, pp. 132–134, (1976), American College of Surgeons.

Marinovich, et al., "Mixtures of Benomyl, Primiphos–Methyl, Dimethoate, Diazinon and Azinphos–Methyl Affect Protein Synthesis in HL–60 Cells Differently", Toxicol., vol. 94, pp 173–185, (1994), Elsevier Science Ireland Ltd.

Menzel, et al., "Effects of some systemic fungicides on viral multiplication", Chemical Abstracts 92:123231, (1979), American Chemical Society.

The Merck Index, Twelfth Edition, "7943: Procodazole", p. 1333, and "9877: Triprolidine", pp. 1660–1661, (1996), Merck Research Laboratories.

The Merck Index, Eighth Edition, "Thiabendazole", p. 1035, (1968), Merck & Co., Inc.

Naim, et al. "Studies in antiparasitic agents. Part II. Synthesis of 5–substituted 2–alkyl(aryl)carbonylaminobenzimidazoles as orally effective anthelmintics", Indian J. Chem., Sect. B, 29B(5), pp. 464–470, (1990), American Chemical Society, (Abstract only).

Nasr et al., "Computer Assisted Structure–Anticancer Activity Correlations of Carbamates and Thiocarbamates", Journal of Pharmaceutical Sciences, pp. 831–836, (1985), American Pharmaceutical Association.

Nene, et al., "Systemic Fungicides", Fungicides in Plant Disease Control, Third Edition, Ch. 9, pp. 208–386, (1993), International Science Publisher.

Niwas, et al. "Possible anthelmintic agents. Synthesis of 4–aryl–2, 5–dimethyl–3–(N,N–disubstituted carbamoyl) furans, substituted isoquinolino [1,2–b]quinazolines and methyl 5(6)–substituted benzimidazole–2–carbamates", Indian J. Chem., Sect. B, 24B(7), pp. 754–760, (1985), American Chemical Society (Abstract only).

Paget et al., "Heterocyclic Substituted Ureas. I. Immunosuppression and Virus Inhibition by Benzimidazoleureas", Journal of Medicinal Chemistry, vol. 12, pp. 1010–1015, (1969), American Chemical Society.

Paget et al., "Heterocyclic Substituted Ureas. I. Immunosuppression and Virus Inhibition by Benzimidazoleureas", Chemical Abstract 72:12644, (1970), American Chemical Society.

Paget et al., "Antiviral and immunization reaction–suppressing compounds containing an N–heterocyclics urea compound", Chemical Abstract 73:87920, (1970), American Chemical Society.

Park, "An Inquiry into the Etiology of Cancer", The American Journal of the Medical Sciences, vol. 115, No. 5., pp. 504–520, (1898), Lippincott Williams & Wilkins.

Private Communication to Dr. Von Hoff from National Institute of Health, National Cancer Society (Sep. 18, 1995).

Rajappa, et al., "A novel synthesis of 5–acylaminobenzimidazole–2–carbamates: Intramolecular regioselective addition to quinone–imides", Tetrahedron Lett., 24(30), pp. 3155–3158, (1983), American Chemical Society (Abstract only).

Rajappa, et al. "Quinone imine route to benzimidazol–2–ylcarbamates. Part 1. Synthesis of open–chain and cyclic 5–acylamino derivatives", J. Chem. Res., Synop., (5), pp. 158–159, (1986), American Chemical Society (Abstract only).

Rajappa, et al., "Selective functionalization in 2–nitro–p–phenylenediamine. Part I. Synthesis of derivatives of 5 – aminobenzimidazole", Indian J. Chem., Sect B., 19B(7), pp. 533–535, (1980), American Chemical Society (Abstract only).

Ram, et al., "Synthesis and Biological Activity of Certain Alkyl 5–(Alkoxycarbonyl)–1H–Benzimidazole–2–carbmates and Realted Derivatives: A New Class of Potential Antineoplastic and Antifilarial Agents", pp. 539–547, (1992), Journal of Medicinal Chemistry, vol. 35, No. 3, American Chemical Society.

Sawhney, et al., "Synthesis of some benzimidazole derivatives as potential anthelmintics", Indian J. Chem., Sect. B, 28B(7), pp. 574–578, (1989), American Chemical Society, (Abstract only).

Setoi et al. "Preparation of benzamide derivatives having a vasopressin antagonistic activity", Chemical Abstract 129:67773, (1998), American Chemical Society.

Sokhanenkova, "Characteristics of the cholinesterase system of ascarids and the effect on it of benzimidazole carbamates", Tr. Gel'mintol. Lab., Akad. Nauk SSSR, 32, pp. 154–159, (1984), American Chemical Society (Abstract only).

Srivastava, et al., "Synthesis of 2,5–disubstituted benzimidazoles, 1,3,4–thiadiazoles and 3,5–diiodosalicylanilides as structural congeners of rafoxanide and closantel", Pharmazie, 45(1), pp. 34–37, (1990), American Chemical Society, (Abstract only).

Stedman's Medical Dictionary, 24th Edition, "Leukemia", pp. 777–778, (1983), Williams & Wilkins.

Tanneberg, et al., "Substituted Benzimidazolecarbmates", (1985), Chemical Abstracts 102:24617, American Chemical Society.

Teicher, et al., "Potentiation of Cytotxic Therapies by TNP–470 and Minocycline in Mice Bearing EMT–6 Mammary Carcinoma", Breast Cancer Research and Treatment, vol. 36, pp 227–236, (1995), Kluwer Academic Publishers.

Thomson, "Fungicides", Agricultural Chemicals Book IV, pp. 154, 121, 123, (1993–1994), Revision Thomson Publications.

Vergieva, "Carbendazim teratogenic activity of rats", Chemical Abstracts 98:66765, (1982), American Chemical Society.

Visen, et al., "Speed of action of methyl 5(6)–[4–(2–pyridyl)]piperazinocarbamoylbenzimidazole–2–carbamate, mebendazole and thiabendazole against experimental hookworm infections", Indian J. Exp. Bio., 25(10), pp. 695–699, (1987), American Chemical Society (Abstract only).

* cited by examiner

COMPOUNDS FOR USE IN THE TREATMENT OF CANCER OR VIRAL INFECTIONS

The present application is a divisional application of U.S. Ser. No. 09/670,170, filed Sep. 26, 2000 now U.S. Pat. No. 6,380,232.

TECHNICAL FIELD

The present invention relates to benzimidazole derivatives and their use for the treatment of cancer or a viral infection in warm blooded animals, particularly in humans and other mammals. The methods may use such a compound in combination with a potentiator or a chemotherapeutic agent.

BACKGROUND OF THE INVENTION

Cancers are a leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents that target especially rapidly dividing cells (both tumor and normal) have been used.

Clearly, the development of materials that would target cancer cells due to some unique specificity for them would be a breakthrough. Alternatively, materials that were cytotoxic to cancer cells while exerting mild effects on normal cells would be desirable.

Human Immunodeficiency Virus (HIV), the etiological agent for AIDS (acquired immune deficiency syndrome), is a member of the lentiviruses, a subfamily of retroviruses. HIV integrates its genetic information into the genome of the host. Most importantly, HIV infects and invades cells of the immune system; it breaks down the body's immune system and renders the patient susceptible to opportunistic infections and neoplasms. HIV-1 is cytopathic for T4 lymphocytes, cells of the immune system that express the cell surface differentiation antigen CD4. In addition to CD4+ T cells, the host range of HIV includes cells of the mononuclear phagocytic lineage, including blood monocytes, tissue macrophages, Langerhans cells of the skin and dendritic reticulum cells within lymph nodes.

Precursor cells in the bone marrow are released into the blood in an immature circulating form known as monocytes. Monocytes use the blood strictly as a transport medium. Once they arrive where they're going to be used, they leave the blood and complete differentiation into macrophages. Cells of the monocyte/macrophage lineage are a major target population for infection with HIV in the body and are thought to provide reservoirs of virus for disseminating infection throughout the body. HIV is also neurotropic, capable of infecting monocytes and macrophages in the central nervous system causing severe neurologic damage. They can interact and fuse with CD4-bearing T cells, causing T cell depletion and thus contributing to the pathogenesis of AIDS.

Progression from HIV infection to AIDS is primarily determined by the effects of HIV on the cells that it infects, including CD4+ T lymphocytes and macrophages. In turn, cell activation, differentiation and proliferation regulate HIV infection and replication in those cells. HIV and other lentiviruses can proliferate in nonproliferating, terminally differentiated macrophages and growth-arrested T lymphocytes. This ability of lentiviruses, including HIV, to replicate in nonproliferating cells, particularly in macrophages, is believed to be unique among retroviruses.

Due to the above-mentioned problems in the art, the present inventors have sought improvements and provide such improvements herein.

Carbendazim, or 2-methoxycarbonylaminobenzimidazole, has been studied as a cancer treatment. See U.S. Pat. No. 5,767,138 issued Jun. 16, 1998 to J. B. Camden. Carbendazim metabolizes in the body through the hydroxylation of the benzene ring, primarily in the 5-position. The metabolite is not as active in the treatment of cancer as the 2-methoxycarbonylaminobenzimidazole. Moreover, this compound is not very soluble. A derivative that maintains the activity of the benzimidazole but is more soluble is highly preferred. It has been found that substituted benzimidazole carbamates, and in particular, those claimed herein are more soluble, yet maintain cytotoxic behavior.

SUMMARY OF THE INVENTION

The compounds of the present invention are represented by the following formula A:

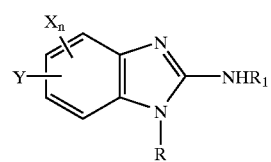

A wherein,
R is hydrogen, —COOR$_2$ or —CONHR$_2$;
R$_1$ is hydrogen, —COOR$_3$ or —CONHR$_3$;
each of R$_2$ and R$_3$ is independently alkyl, haloalkyl, alkenyl, haloalkenyl, cycloalkyl, cycloalkalkyl, heterocycloalkyl, heterocycloalkalkyl, substituted or unsubstituted benzyl, hydroxyalkyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;
each of X and Y is independently hydrogen, alkyl, alkenyl, cycloalkyl, haloalkyl, haloalkenyl, bromo, chloro, fluoro, nitro, or amino; and
n is 1, 2 or 3.
The benzyl group may optionally be substituted with one or more nitro, carboxy, hydroxy, alkyl, alkoxy, or halide substituents.

Pharmaceutically acceptable salts of the benzimidazole derivatives of formula A are also included in the present invention. Further included in the invention are the prodrugs of the compounds of formula A.

In one presently preferred embodiment of the invention, the benzimidazole derivatives of the invention are of the formula A-1 or A-2:

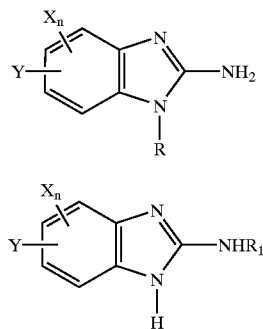

and more preferably the compounds are of formula A-1 or A-2 where each of X and Y is hydrogen.

In another presently preferred embodiment of the invention, the benzimidazole derivatives are of the formula A-3:

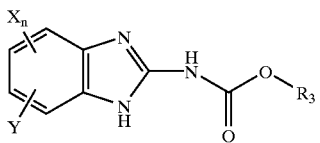

and more preferably, the compounds are of formula A-3 where X is hydrogen and Y is hydrogen or halogen; the halogen is preferably chloro.

In another presently preferred embodiment of the invention, the benzimidazole derivatives are of the formula A-4:

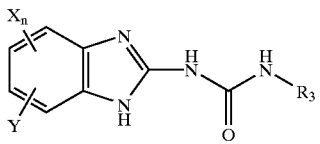

and more preferably, the compounds are of formula A-4 where X is hydrogen and Y is hydrogen or halogen; the halogen is preferably chloro.

Methods are provided by the present invention for treatment of warm blooded animals, and in particular, humans and other mammals, that are affected by cancer or viral infection, the methods comprising administering a therapeutically effective amount of a benzimidazole derivative of formula A, or a salt or a prodrug thereof, to the animal.

DETAILED DESCRIPTION OF THE INVENTION

A. Definitions

The term "alkyl" refers to a fully saturated monovalent hydrocarbon radical of 1 to 12 carbon atoms. It may be straight-chain or branched. Preferred are those alkyl groups containing 1 to 10 carbon atoms, with 2 to 8 carbon atoms particularly preferred.

The term "alkenyl" refers to an unsaturated monovalent hydrocarbon radical of 2 to 12 carbon atoms containing only carbon and hydrogen and having one or more double bonds. It may be straight-chain or branched. Preferred are those alkenyl groups containing 2 to 10 carbon atoms, with 2 to 8 carbon atoms particularly preferred.

The term "alkoxy" means the group —OR' wherein R' is alkyl. Preferred are alkoxy groups having 1 to 10 carbon atoms, more preferably 2 to 8 carbon atoms.

The term "alkoxyalkyl" refers to an alkoxy group covalently attached to an alkyl group. The alkoxy group contains from 1 to 12, preferably from 1 to 6 carbon atoms. The alkoxy group may be substituted with one or more hydroxyl groups (an "hydroxyalkoxyalkyl") or with one or more halogen atoms (a "haloalkoxyalkyl"); preferably the hydroxyl or halogen is on the terminal end of the alkoxyalkyl substituent.

The term "poly(alkoxy)alkyl" denotes 2 to 200, preferably 2 to 20, alkoxy groups covalently linked in either a linear or a branched configuration and attached to an alkyl group. Linear poly(alkoxy)alkyl moieties have a structure such as —(CH$_2$)$_m$—O—(CH$_2$)$_m$—O—(CH$_2$)$_m$—O—(CH$_2$)$_m$—...
—O—C$_m$H$_{2m+1}$, where "m" is an integer, the same or different along the length of the chain. Branched moieties have two or more (—O—(CH$_t$)$_m$—) groups bound to a common third (—O—(CH$_t$)$_m$—) group, where "t" has a value that is independently selected from 0, 1 and 2 for each (CH$_t$)$_m$ group. Linear configurations are preferred. The number of repeating (—O—(CH$_t$)$_m$—) groups within a substituent may be up to 200, preferably from 2 to 20, more preferably from 2 to 7, and most preferably is 2–5. The individual alkoxy groups may be the same or different, and individual alkoxy groups preferably contain from 1 to 6 carbon atoms each, and most preferably from 1 to 3 carbon atoms each. A presently preferred poly(alkoxy)alkyl is —(CH$_2$)$_y$—(OCH$_2$CH$_2$)$_x$—OCH$_3$ or —(CH$_2$)$_y$—(OCH$_2$CH$_2$)$_x$—OCH$_2$CH$_3$, where y=1–4 and x=1–100, preferably 1–10, and more preferably, 2–5. The individual alkoxy groups may be substituted with one or more hydroxyl groups (an "hydroxypoly (alkoxy)alkyl") or with one or more halogen atoms (a "halopoly(alkoxy)alkyl"); preferably the hydroxyl or halogen is on the terminal end of the poly(alkoxy)alkyl substituent.

"Heterocyclo" designates a heterocyclic group; that is, a closed-ring structure, usually of either 5 or 6 members, in which one or more of the atoms in the ring is an element other than carbon, such as for example sulfur, nitrogen, or oxygen. A heterocyclic group may be, but is not limited to, pyridine, pyrrole, furan, thiophene, morpholine, and purine, optionally substituted with one or more nitro, carboxy, sulfonic acid, hydroxy, alkyl, alkoxy, or halide substituents.

The term "amino" refers to primary amines (—NH$_2$), secondary amines (—NHR'), and tertiary amines (—NR'R"), where R' and R" are the same or different substituent groups, such as alkyl, alkenyl, halogen, hydroxy, and the like.

"Independently" signifies that two or more of the groups immediately preceding the term are either identical or different; i.e., selection of one from the list following the term does not affect selection of the other(s).

"Substituted" encompasses both single and multiple substitutions, the latter including multiple substitutions by the same substituent as well as mixtures of different substituents.

The term "optional" or "optionally" means that the subsequently described event or circumstance may or may not occur, and that the description includes instances in which said event or circumstance occurs and instances in which it does not. For example, "optionally substituted phenyl" means that the phenyl may or may not be substituted and that the description includes both unsubstituted phenyl and phenyl wherein there is substitution. As another example, "optionally" followed by "converting the free base to the acid addition salt" means that such conversion may or may not be carried out in order for the process described to fall within the invention, and the invention includes those processes wherein the free base is converted to the acid addition salt and those processes in which it is not.

As used herein, "a therapeutically effective amount" means the concentration or quantity or level of the compound of the present invention that can attain a particular medical end, such as control or destruction of cancer cells, virally-infected cells, or viruses without producing unacceptable toxic symptoms. The term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the type of mammal being treated, the duration of the treatment, the nature of concurrent therapy (if any), and the specific formulations employed and the structure of the compounds or its salts.

As used herein, a "pharmaceutical addition salt" or "pharmaceutically acceptable salt" is a salt of the benzimidazole derivative compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and others known to those of ordinary skill in the art.

As used herein, the term "prodrug" refers to a form of a benzimidazole derivative compound that has minimal therapeutic activity until it is converted to its desired biologically active form. A prodrug is a compound having one or more functional groups or carriers covalently bound thereto, which functional groups or carriers are removed from the compound by metabolic processes within the body to form the respective bioactive compound.

As used herein, the term "metabolite" refers to the breakdown or end product of a benzimidazole derivative compound or its salt produced by metabolism or biotransformation in the animal or human body; e.g., biotransformation to a more polar molecule such as by oxidation, reduction, or hydrolysis, or to a conjugate (see Goodman and Gilman, "The Pharmacological Basis of Therapeutics" 8$^{th}$ Ed., Pergamon Press, Gilman et al. (eds.). 1990 for a discussion of biotransformation). As used herein, the metabolite of a benzimidazole derivative compound or its salt may be the biologically active form of the compound in the body. An assay for activity of a metabolite of a benzimidazole derivative of the present invention is known to one of skill in the art in light of the present disclosure, for example, testing for efficacy against a virus in vitro or in vivo.

As used herein, a "subject in need thereof" is a warm blooded animal having cancer or having a viral infection.

As used herein, "cancer" refers to all types of cancers, or neoplasms or benign or malignant tumors. In one embodiment, those cancers that attack normal healthy blood cells or bone marrow are contemplated by the present invention. Preferred cancers for treatment using methods provided herein include carcinoma, sarcoma, lymphoma, or leukemia. By "carcinoma" is meant a benign or malignant epithelial tumor and includes, but is not limited to, breast carcinoma, prostate carcinoma, non-small cell lung carcinoma, colon carcinoma, CNS carcinoma, melanoma carcinoma, ovarian carcinoma, or renal carcinoma. A preferred host is a human host.

A "viral infection" as used herein means an infection due to a DNA virus or an RNA virus (retrovirus). Examples of a double-stranded DNA virus are the Herpes virus and the influenza virus. Human inmmunodeficiency virus (HIV) is a prototype for retroviruses, i.e., viruses that use reverse transcription to replicate. However, certain DNA viruses use, in part, reverse transcription mechanisms to replicate such as, for example, the Hepatitus B virus. "Viruses" include retroviruses such as HIV or HTLV, influenza, rhinoviruses, herpes, hepatitis, or the like.

As used herein, a benzimidazole derivative of formulas A and A-1 through A-4, or a pharmaceutical salt thereof or a prodrug thereof, are "compounds of the present invention." Such compounds are further set forth under B infra.

As used herein, "chemotherapeutic agents" includes DNA-interactive agents, antimetabolites, tubulin-interactive agents, hormonal agents and others, such as asparaginase or hydroxyurea, and are as further set forth under D infra.

As used herein, "potentiators" are materials that affect the immune system or enhance the effectiveness of a compound of the present invention and are further set forth under E herein.

Following long-standing patent law convention, the terms "a" and "an" mean "one or more" when used in this application, including the claims.

B. Benzimidazole Derivatives

The benzimidazole derivatives of the present invention are those of formula A, as set forth above. In one embodiment of the invention, presently preferred compounds are those of formulas A-1 and A-2. In another embodiment, presently preferred compounds are those of formulas A-3 and A-4.

Pharmaceutically acceptable salts of the benzimidazole compounds are considered within the scope of compounds of the present invention. They are salts with an organic or inorganic acid. Preferred acid addition salts are chlorides, bromides, sulfates, nitrates, phosphates, sulfonates, formates, tartrates, maleates, malates, citrates, benzoates, salicylates, ascorbates, or the like. Such salts may be synthesized from the compound of the present invention, or derivative thereof, that contains a basic or acidic moiety, by conventional chemical methods. Generally, such salts may be prepared by reacting a free acid or base form of the compound, or derivative thereof, with a stoichiometric amount of the appropriate base or acid in water or in an organic solvent, or in a mixture of the two. Generally, nonaqueous media like ether, ethyl acetate, ethanol, isopropanol, or acetonitrile are preferred. Further suitable salts may be found in *Remington: The Science and Practice of Pharmacy*, 19th ed., Mack Publishing Company, Easton, Pa., 1995, p. 1457.

Pharmaceutically acceptable salts of the compounds of the present invention include conventional non-toxic salts or the quaternary ammonium salts of the compounds or derivatives formed, for example, from non-toxic inorganic or organic acids. For example, such conventional non-toxic salts include those derived from inorganic acids such as hydrochloric, hydrobromic, sulfuric, sulfamic, phosphoric, nitric, or the like; and salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, or the like. Preferred acid addition salts are chlorides, bromides, sulfates, nitrates, phosphates, sulfonates, formates, tartrates, maleates, malates, citrates, benzoates, salicylates, ascorbates, or the like. A presently preferred salt is the hydrochloride salt.

Further included within the scope of the compound, or salts thereof, useful for the present invention are prodrugs thereof. As used herein, a "prodrug" is a drug covalently bonded to a carrier wherein release of the drug occurs in vivo when the prodrug is administered to a mammalian subject. Prodrugs of the compounds of the present invention are prepared by modifying functional groups present in the compounds in such a way that the modifications are cleaved, either in routine manipulation or in vivo, to yield the desired compound. Prodrugs include compounds wherein hydroxy, amine, or sulfhydryl groups are bonded to any group that, when administered to a mammalian subject, is cleaved to form a free hydroxyl, amino, or sulfhydryl group, respectively. Examples of prodrugs include, but are not limited to, acetate, formate, or benzoate derivatives of alcohol or amine functional groups in the compounds of the present invention; phosphate esters, dimethylglycine esters, aminoalkylbenzyl esters, aminoalkyl esters or carboxyalkyl esters of alcohol or phenol functional groups in the compounds of the present invention; or the like.

Synthetic Reaction Parameters

The terms "solvent", "inert organic solvent" and "inert solvent" mean a solvent that is passive or non-reactive under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine, and the like). Unless specified to the contrary, the solvents used in the reactions of the present invention are inert organic solvents.

The reaction temperature can vary widely depending on the reactivity of the reactants. However, the temperature should not be so high as to decompose the reactants or so low as to cause inhibition of the condensation or freezing of the solvent. Unless specified to the contrary, the reactions described herein take place at atmospheric pressure over a temperature range from the temperature of dry ice to about 100° C., more preferably from about 10°C. to about 50° C., and most preferably at "room" or "ambient" temperature ("RT"), e.g. about 20° C.

Unless otherwise specified, the reaction times and conditions are intended to be approximate.

The time required for the reactions herein will depend to a large extent on the temperature being used and the relative reactivities of the starting materials. Therefore, the reaction time can vary greatly, for example from about five minutes to about two days. Various known techniques such as different types of chromatography, especially thin layer chromatography ("TLC"), gas chromatography ("GC"), or spectroscopy can be used to follow the progress of the reaction by the disappearance of the starting compound(s).

Isolation and purification of the compounds and intermediates described herein can be effected, if desired, by any suitable separation or purification procedure such as, for example, filtration, extraction, crystallization, column chromatography, thin-layer chromatography, thick-layer chromatography, centrifugal chromatography, or preparatory HPLC, or a combination of these procedures. Specific illustrations of suitable separation and isolation procedures can be found by reference to the examples hereinbelow. However, other equivalent separation or isolation procedures can, of course, also be used.

Synthesis of Compounds of Formula A

The compounds of the invention are prepared by modification to the benzimidazole nucleus:

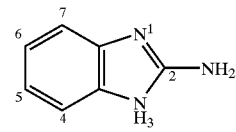

In one synthetic process, commercially available 2-aminobenzimidazole (101) can be reacted with a variety of chloroformates or isocyanates in pyridine to form, respectively, carbamates (105) or ureas (103) at the N3 position. In this manner, N3-substituted benzimidazole derivatives of formula A-1 (105) or A-2 (103) with a free 2-amino group are synthesized (Reaction Scheme 1).

Reaction Scheme 1:

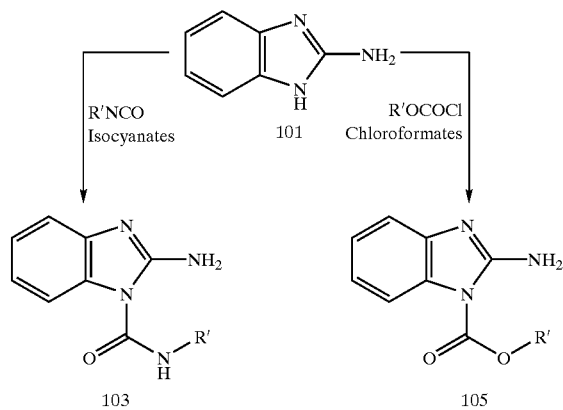

By heating the N3-acyl analogs (103, 105) in pyridine, the acyl groups can be induced to migrate to the 2-amino position to give benzimidazole derivatives of formula A-3 or A-4 (205 and 203, respectively) (Reaction Scheme 2).

Reaction Scheme 2:

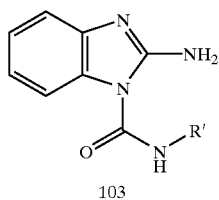
103

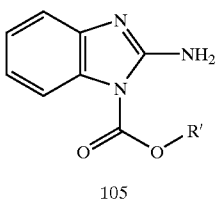
105

Pyridine, Heat

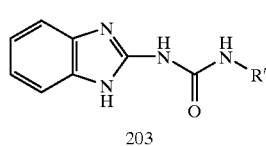
203

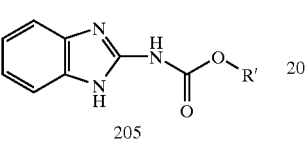
205

Where it is desired to synthesize a compound of formula A having a chlorine atom at the 5(6) position, 4-chloro-1, 2-phenylenediamine 301 is condensed with cyanogen bromide (Zou, R. et al., *J. Med. Chem.* 40:811–818 (1997)) to give the corresponding chloro 2-aminobenzimidazole 303. The benzimidazole 303 can then be heated with an isocyanate in pyridine to form the chloro 2-aminourea analogs 305 (Reaction Scheme 3).

Reaction Scheme 3:

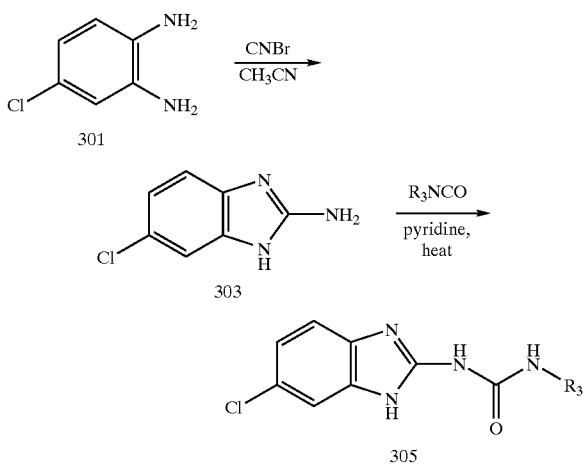

In another method for preparing the compounds of formula A-3 or A-4, the commercially-available fungicide methyl 2-aminobenzimidazole carbamate (carbendazim, 401) is treated with an appropriate alcohol or amine with or without added toluene as the solvent in the presence of aluminum isopropoxide catalyst to give new carbamates (403) and ureas (405), respectively (Reaction Scheme 4).

Reaction Scheme 4:

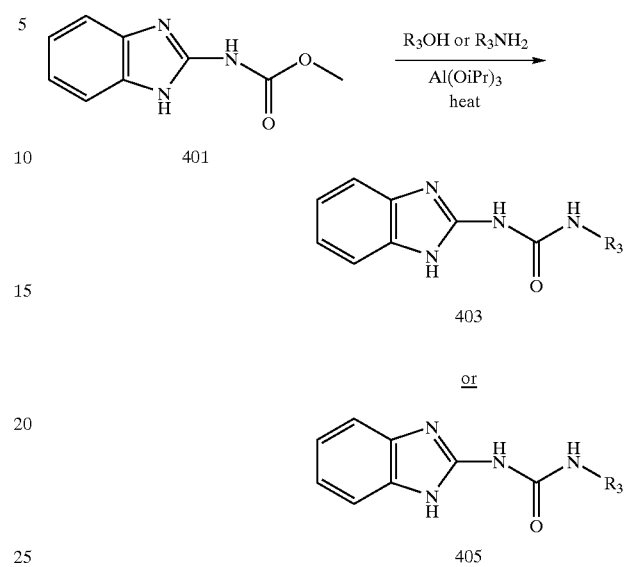

Presently Preferred Embodiments

In one embodiment of the present invention, presently preferred benzimidazole derivatives are those where $R_1$ and X are hydrogen, and Y is hydrogen or chloro and is in the 5(6)-position. Further preferred are those compounds where $R_1$, X and Y are hydrogen and R is selected from those groups listed in Table 1: Solubility is based on a standard measure used in medicinal chemistry, the octanol-water partition coefficient, LogP, Lower Log) values indicate higher aqueous solubility. There are a variety of methods to estimate this value for a proposed structure using computer calculations. The below LogP solubility values were determined using the atom typing method of Ghose, Pritchett et a. (*J. Comput. Chem* 9(1): 80–90, 1988). Carbendazim has a LogP of 1.302.

TABLE 1

| Cpd. No. | R | LogP |
|---|---|---|
| 1-1 | —COOCH$_2$CH=CH$_2$ | 2.408 |
| 1-2 | —COOCH$_2$CCl$_3$ | 3.202 |
| 1-3 | —CONHCH$_2$CH$_2$Cl | 1.721 |
| 1-4 | —CONHCH$_2$Ph | 2.794 |
| 1-5 | —COOCH$_2$Ph | 3.444 |
| 1-6 | —CONHCH$_2$CH$_2$CH$_3$ | 1.829 |
| 1-7 | —COOCH$_2$CH$_3$ | 2.479 |
| 1-8 | —COOCH$_2$CH$_2$CH$_2$N(CH$_3$)$_2$ | — |
| 1-9 | —CONHCH$_2$Ph(-2-OH) | — |
| 1-10 | —COOCH$_2$CH$_2$-morpholino | — |
| 1-11 | —COOCH(CH3)(cyclopropyl) | — |

In another embodiment of the invention, presently preferred benzimidazole derivatives are those where R is hydrogen, X is hydrogen, and Y is hydrogen or chloro and is in the 5(6)-position Further preferred are those compounds where R and X are hydrogen, Y is hydrogen or chloro in the 5(6) position, and $R_1$ is selected from those groups listed in Table 2:

TABLE 2

| Cpd. No. | R | LogP |
|---|---|---|
| 2-1 | —CONHCH$_2$CH$_2$N(CH$_3$)$_2$ | 0.631 |
| 2-2 | —COOCH$_2$CH=CH$_2$ | 2.042 |
| 2-3 | —COO(CH$_2$CH$_2$O)$_2$CH$_2$CH$_3$ | 1.315 |
| 2-4 | —CONHCH$_2$CH$_2$OCH$_2$CH$_2$OH | 0.044 |
| 2-5 | —COOCH$_2$CH$_2$OCH$_2$CH$_2$Cl | 1.841 |
| 2-6 | —COOCH$_2$CH$_2$Cl | 2.005 |
| 2-7 | —COOCH$_2$CH$_2$OCH$_2$CH$_2$OH | 0.694 |
| 2-8 | —COOCH$_2$CH$_2$CH$_3$ | 2.113 |
| 2-9 | —COOCH$_2$Ph | 3.078 |
| 2-10 | —CONHCH$_2$CH$_2$Cl | 1.355 |
| 2-10* | —CONHCH$_2$CH$_2$Cl | 1.873 |
| 2-11 | —CONHCH$_2$Ph | 2.428 |
| 2-12 | —CONHCH$_2$CH$_2$CH$_3$ | 1.463 |
| 2-12* | —CONHCH$_2$CH$_2$CH$_3$ | 1.981 |
| 2-13 | —CONHCH$_3$ | — |
| 2-13* | —CONHCH$_3$ | 1.170 |
| 2-14 | —CONHCH$_2$Ph(-2-OH) | — |
| 2-15 | —COOCH$_2$CH$_2$-morpholino | — |
| 2-16 | —COOCH(CH3)(cyclopropyl) | — |

*Y =Cl, at the 5(6) position

C. Screening Assays

Screening assays for determining those cancers susceptible to treatment using compounds of the present invention include incubating cell line models representing specific cancers as set forth, for example, by the National Cancer Institute, in the presence and absence of such compounds. Viability of cells may be determined by the MTT assay (Promega Corp., Madison, Wis. 53711), or the SRB (sulforhodamine B) assay (Skehan, et al., *JNCI*, 82:13,1107, 1990). Susceptibility to said compounds exists when viability in the presence of a compound of the present invention is less than viability in the absence of such compound.

Exemplary cell line models representing specific cancers include, but are not limited to, the following:

Non-small cell lung cancer: NCIH23, NCIH324, NCIH522, A549/ATCC, A549(ASC), CALU1, EKVX, NCIH125M, NCIH226, NCIH520, SKMES1, NCIH322M, NCIH358M, NCIH460, NCIH292, HOP62, HOP18, HOP19, HOP92, LXFL 529, SW1573, LXFS 650L, ML1019, ML1076, ML1045, or UABLG22;

Small cell lung cancer: NCIH69, NCIH146, NCIH82, NCIH524, DMS 114, DMS 273, HOP27, SHP77, or RHOS;

Colon cancer: HT29, HCC2998, HCT116, LOVO, SW1116, SW620, COLO 205, DLD1, WIDR, COLO 320DM, HCT15, CXF 280, KM12, KM20L2, COLO 741, CXF 264L, COLO 746, UABC02, MLI059, CAC02, HT29/PAR, HT29/MDR1, or NB4;

Breast cancer: MCF7, MCF7/ADRRES, ZR751, ZR7530, MDAMB231/ATCC, HS 578T, UISOBCA1, MCF7/ATCC, SKBR3, MDAMB435, MDAN, BT549, T47D, MDAMB231, MAXF 401, BT474, or MDAMB468;

Ovarian cancer: OVCAR3, OVCAR4, OVCAR5, OVCAR8, A2780, IGROV1, SKOV3, OVXF 899, A1336, or ES2;

Leukemia: P388, P3888/ADR, CCRFCEM, CCRFSB, K562, MOLT4, L1210, HL60(TB), RPM18226, SR, or K562/ADR;

Fibroblast: IMR90, or CCD19LU;

Renal cancer: UO31, SN12C, SN12S1, SN12K1, SN12L1, SN12A1, A498, A704, CAKI1, RXF 393, RXF631, 7860, SW156, TK164, 769P, SS78, ACHN, TK10, RXF 486L, UOK57, or UOK57LN;

Melanoma: LOX IMVI, MALME3M, RPMI7951, SKMEL2, SKMEL5, SKMEL28, SKMEL31, UCSD 242L, UCSD 354L, M14, M19MEL, UACC62, UACC257, MEXF 514L, or UABMEL3;

Prostate cancer: PC3, PC3M, DU145, LNCAP, 1013L, UMSCP1, WIS, JE, RER, MRM, DHM, AG, RB, RVP, FC, WAE, DB/SMC, JCA1, ND1, WMF, TSUPRI, JECA, GDP, T10, WBW, RVP1, or WLL;

CNS cancer: SNB7, SNB19, SNB44, SNB56, SNB7S, SNB78, U251, TE671, SF268, SF295, SF539, XF 498, SW 1088, SW 1783, U87 MG, SF767, SF763, A172, or SMSKCNY;.

Bone/muscle: A204/ATCC, OHS, TE85, A673, CHA59, MHM 25, RH18, RH30, or RD; and

Lymphoma: AS283, HT, KD488, PA682, SUDHL7, RL, DB, SUDHL1, SUDHL4, SUDHL10, NUDUL1, or HUT 102.

D. Chemotherapeutic Agents

Chemotherapeutic agents are generally grouped as DNA-interactive agents, antimetabolites, tubulin-interactive agents, hormonal agents, other agents such as asparaginase or hydroxyurea, and agents as set forth in Table 3. Each of the groups of chemotherapeutic agents can be further divided by type of activity or compound. Chemotherapeutic agents used in combination with a compound of the present invention, or salts thereof of the present invention may be selected from any of these groups but are not limited thereto. For a detailed discussion of the chemotherapeutic agents and their method of administration, see Dorr, et al, *Cancer Chemotherapy Handbook*, 2d edition, pages 15–34, Appleton & Lange (Connecticut, 1994) herein incorporated by reference.

DNA-interactive agents include alkylating agents, e.g. cisplatin, cyclophosphamide, altretamine; DNA strand-breakage agents, such as bleomycin; intercalating topoisomerase II inhibitors, eg., dactinomycin and doxorubicin); nonintercalating topoisomerase II inhibitors such as, etoposide and teniposide; and the DNA minor groove binder plicamydin, for example.

The alkylating agents form covalent chemical adducts with cellular DNA, RNA, or protein molecules, or with smaller amino acids, glutathione, or similar chemicals. Generally, alkylating agents react with a nucleophilic atom in a cellular constituent, such as an amino, carboxyl, phosphate, or sulfhydryl group in nucleic acids, proteins, amino acids, or in glutathione. The mechanism and the role of these alkylating agents in cancer therapy is not well understood.

Typical alkylating agents include, but are not limited to, nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine.

DNA strand breaking agents include bleomycin, for example.

DNA topoisomerase II inhibitors include the following intercalators, such as amsacrine, dactinomycin, daunorubicin, doxorubicin (adriamycin), idarubicin, and mitoxantrone; nonintercalators, such as etoposide and teniposide, for example.

A DNA minor groove binder is plicamycin, for example.

Antimetabolites interfere with the production of nucleic acids by one of two major mechanisms. Certain drugs inhibit production of deoxyribonucleoside triphosphates that are the immediate precursors for DNA synthesis, thus inhibiting DNA replication. Certain of the compounds are analogues of purines or pyrimidines and are incorporated in anabolic nucleotide pathways. These analogues are then substituted into DNA or RNA instead of their normal counterparts.

Antimetabolites useful herein include, but are not limited to, folate antagonists such as methotrexate and trimetrexate; pyrimidine antagonists, such as fluorouracil, fluorodeoxyuridine, CB3717, azacitidine, cytarabine, and floxuridine; purine antagonists include mercaptopurine, 6-thioguanine, fludarabine, pentostatin; and ribonucleotide reductase inhibitors include hydroxyurea.

Tubulin interactive agents act by binding to specific sites on tubulin, a protein that polymerizes to form cellular microtubules. Microtubules are critical cell structure units. When the interactive agents bind the protein, the cell can not form microtubules. Tubulin interactive agents include vincristine and vinblastine, both alkaloids and paclitaxel (Taxol), for example.

Hormonal agents are also useful in the treatment of cancers and tumors. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Further agents include the following: hydroxyurea appears to act primarily through inhibition of the enzyme ribonucleotide reductase, and asparaginase is an enzyme which converts asparagine to nonfunctional aspartic acid and thus blocks protein synthesis in the tumor.

Taxol (paclitaxel) is a preferred chemotherapeutic agent.

A listing of currently available chemotherapeutic agents according to class, and including diseases for which the agents are indicated, is provided as Table 3.

TABLE 3

Neoplastic Diseases[1] for which Exemplary Chemotherapeutic agents are Indicated

| Class | Type of Agent | Name | Disease[2] |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan | Multiple myeloma, breast, ovary |
| | | Chlorambucil | Chronic lymphocytic leukemia, primary macroglobulinemia, Hodgkin's disease, non-Hodgkin's lymphomas |
| | | Estramustine | Prostate |
| | Ethylenimines and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine Procarbazine Aziridine | Malignant melanoma, Hodgkin's disease, soft-tissue sarcomas |
| Antimetabolites | Folic Acid Analogs | Methotrexate Trimetrexate | Acute lymphocytic leukemia, choriocarcinoma, mycosis fungoides, breast, head and neck, lung, osteogenic sarcoma |
| | Pyrimidine Analogs | Fluorouracil Floxuridine | Breast, colon, stomach, pancreas, ovary, head and neck, urinary bladder, premalignant skin lesions (topical) |
| | | Cytarabine Azacitidine | Acute granulocytic and acute lymphocytic leukemias |
| | Purine Analogs and Related Inhibitors | Mercaptopurine | Acute lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, |

TABLE 3-continued

Neoplastic Diseases[1] for which Exemplary Chemotherapeutic agents are Indicated

| Class | Type of Agent | Name | Disease[2] |
|---|---|---|---|
| | | Vindesine | rhabdomyosarcoma, Hodgkin's disease, non-Hodgkin's lymphomas, small-cell lung<br>Vinca-resistant acute lymphocytic leukemia, chronic myelocytic leukemia, melanoma, lymphomas, breast |
| | Epipodophyllotoxins | Etoposide<br>Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| | | Doxorubicin<br>4'-Deoxydoxorubicin | Soft-tissue, osteogenic, and other sarcomas; Hodgkin's disease non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | L-Asparaginase | Acute lymphocytic leukemia |
| | Taxanes | Docetaxel | Breast, ovarian |
| | Taxoids | Paclitaxel | |
| | Biological Response Modifiers | Interferon Alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin<br>Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane<br>Aminoglutethimide | Adrenal cortex<br>Breast |
| Hormones and Antagonists | Adrenocorti-costeroids | Prednisone | Acute and chronic lymphocytic leukemias, non-Hodgkin's lymphomas, Hodgkin's disease, breast |
| | Progestins | Hydroxy-progesterone caproate<br>Medroxy-progesterone acetate<br>Megestrol acetate | Endometrium, breast |
| | Estrogens | Diethylstil-bestrol<br>Ethinyl estradiol | Breast, prostate |
| | Antiestrogen | Tamoxifen | Breast |
| | Androgens | Testosterone propionate Fluoxymesterone | Breast |
| | Antiandrogen | Flutamide | Prostate |
| | Gonadotropin-releasing hormone analog | Leuprolide<br>Goserelin | Prostate, Estrogen-receptor-positive breast |

[1]Adapted from Calabresi, P., and B.A. Chabner, "Chemotherapy of Neoplastic Diseases" Section XII, pp 1202–1263 in: Goodman and Gilman's The Pharmacological Basis of Therapeutics, Eighth ed., 1990 Pergamin Press, Inc.; and Barrows, L.R., "Antineoplastic and Immunoactive Drugs", Chapter 75, pp 1236–1262, in: Remington: The Science and Practice of Pharmacy, Mack Publishing Co. Easton, PA, 1995; both references are incorporated by reference herein, in particular for treatment protocols.
[2]Neoplasms are carcinomas unless otherwise indicated.

E. Potentiators

A "potentiator," as used herein, is a material that improves or increases the efficacy of the benzimidazole derivatives or a salt or a prodrug thereof, or that acts on the immune system as an immunomodulator. Potentiators can be used in combination with a compound of the present invention. A potentiator may be an antiviral agent. One such potentiator is triprolidine or its cis-isomer. Triprolidine is described in U.S. Pat. No. 5,114,951 (1992, the patent is incorporated by reference herein). A further potentiator is procodazole, (also named 1H-benzimidazole-2-propanoic acid, or β-(2-benzimidazole) propionic acid or 2-(2-carboxyethyl) benzimidazole or propazol). Procodazole is a non-specific immnunoprotective agent active against viral and bacterial infections and may be used in combination with the compounds set forth herein. Procodazole is effective with a compound of the present invention, alone in treating cancers, tumors, leukemia or viral infections, or combined with a chemotherapeutic agent.

Further potentiators include, but are not limited to, propionic acid, salts thereof, or esters thereof; antioxidant vitamins such as vitamins A, C, E, or beta-carotene; abacavir; AL-721 (lipid mixture); amprenavir; Amphotericin B methyl ester, Ampligen (mismatched RNA); anti-AIDS antibody; anti-human interferon-α antibody; anti-AIDS antibody, ascorbic acid and derivatives thereof; AS-101 (heavy metal based immnunostimulant); azidothymidine; β-interferon; Bropirimine; butylated hydroxytoluene; Ciamexon, Cimetidine; CL-246,738, colony stimulating factors, including GM-CSF; Creme Pharmatex (benzalkonium chloride); CS-82 (5-unsubstituted derivative of Zidovudine); Cyclosporin; D-penicillamine (3-mercapto- D-valine); delavirdine; dextran sulphate; dinitrochlorobenzene; efavirenz; erythropoietin; Foscarnet (trisodium phosphonoformate); fusidic acid; ganciclovir, glucan; glycyrrhizin, HPA-23 (ammonium-21-tungsto-9-antimonate); human immunevirus antiviral; hyperimmnune gamma-globulin, IMREG-1, IMREG-2; indinavir; interferon-α; interferon-gamma; interleukin-1 or interleukin-2; isoprinosine; Krestin; LC-9018; lamivudine; lentilart; LF-1695; methionine-enkephalin; Minophagen C; muramyl tripeptide; naltrexone; relfinavir; Neutropin; nevirapine; Nonoxinol; Ornidyl (eflornithine); non-nucleoside inhibitors of reverse transcriptase; nucleoside analogues (ddA, ddC, ddI, ddT, ddG, AZT, and the like); pentamidine isethionate; Phenytoin; polymannoacetate; Peptide T (octapeptide sequence); protease inhibitors; Ribavirin; Rifabutin (ansamycin); ritonavir; RNA immunomodulator; rsT4 (recombinant soluble T4); saquinavir; shosaikoto and ginseng; SK-818 (germanium-derived antiviral); sodium diethylthiocarbarmate; stavudine; stearic acid derivative; suramin and analogues thereof; thymic humoral factor, TP-5; Thymosin fraction 5 and Thymosin 1; Thymostimulin; TNF (tumor necrosis factor), vitamin B preparations; Trimetrexate; UA001; alpha-interferon; or acyclovir, for example.

A compound, or a salt or a prodrug thereof, of the present invention may be combined with a potentiator and with a chemotherapeutic agent in the methods of the present invention.

F. Dosage

Any suitable dosage may be administered in the methods of the present invention. The compound or salt or prodrug thereof chosen for a particular application, the carrier and the amount will vary widely depending on the species of the warn blooded animal or human, the type of cancer, or the particular viral infection being treated, and depending upon the effective inhibitory concentrations observed in trial studies. The dosage administered will, of course, vary depending upon known factors, such as the pharmacodynamic characteristics of the particular compound, salt, or combination and its mode and route of administration; the age, health, or weight of the subject; the nature and extent of symptoms; the metabolic characteristics of the drug and patient, the kind of concurrent treatment; the frequency of treatment; or the effect desired.

Generally a dosage of as little as about 1–2 milligram (mg) per kilogram (kg) of body weight is suitable, but preferably as little as 10 mg/kg and up to about 10,000 mg/kg may be used. Preferably, a dosage from 15 mg/kg to about 5000 mg/kg is used. Most preferably, the dose is between 150 mg/kg to about 1000 mg/kg. Doses useful in the treatment of cancer or viral infections are 250 mg/kg, 500 mg/kg, 800 mg/kg, 1000 mg/kg, 1500 mg/kg, 2500 mg/kg, 3500 mg/kg, 4000 mg/kg, 5000 mg/kg, or 6000 mg/kg. Any range of doses can be used. Generally, a compound, salt thereof, prodrug thereof, or combination of the present invention can be administered on a daily basis one or more times a day, or one to four times a week, either in a single dose or separate doses during the day. Twice-weekly dosing over a period of at least several weeks is preferred, and often dosing will be continued over extended periods of time and possibly for the lifetime of the patient. However, the dosage and the dosage regimen will vary depending on the ability of the patient to sustain the desired and effective plasma levels of the compounds of the present invention, or salt or prodrug thereof, in the blood.

The compound, salt thereof, prodrug thereof, or combination may be micronized or powdered so that it is more easily dispersed and solubilized by the body. Processes for grinding or pulverizing drugs are well known in the art. For example, a hammer mill or similar milling device can be used. The preferred particle size is less than about 100μ and preferably less than 50μ.

Intravenously, the most preferred doses may range from about 1 to about 10 mg/kg/minute during a constant rate infusion.

The dosage for humans is generally less than that used in mice and is typically about 1/12 of the dose that is effective in mice. Thus, if 500 mg/kg was effective in mice, a dose of 42 mg/kg would be used in humans. For a 60 kg man, this dose would be 2520 mg.

The compounds and salts and prodrugs thereof of the present invention are generally safe. The $LD_{50}$ is high, about 1500 mg/kg given orally in mice and there are no special handling requirements. The compounds can be given orally, and since they are not very soluble, they are preferably given in tablet form or as a suspension. Alternatively, when micronized to sufficiently small size, they may be and preferably are given as an injection.

The compounds and salts and prodrugs thereof of the present invention may be administered in a unit dosage form which may be prepared by any methods known to one of skill in the art in light of the present disclosure. Unit dosages may include from 1 milligram to 1000 milligrams of active ingredient. Preferably the dosage unit will contain from about 10 mg to about 500 mg active ingredient. The active ingredient is generally present in an amount of about 0.5% to about 95% by weight based on the total weight of the dosage unit.

For intravenous use, preferred dosages may range from about 1 to about 10 mg/kg/minute during a constant rate infusion.

A dosage unit may comprise a single compound, or mixtures thereof, with other compounds or other cancer- or viral-inhibiting compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site. The range and ratio of benzimidazole derivative, or salt or prodrug thereof, to chemotherapeutic agent or to potentiator will depend on the type of cancer or viral infection being treated and the particular chemotherapeutic agent or potentiator.

G. Formulations

Formulations of the present invention include the compound of the present invention, a salt thereof or a prodrug thereof and, optionally, a chemotherapeutic agent and, optionally, a potentiator, generally mixed with a pharmaceutically acceptable carrier. A "pharmaceutical carrier" is a pharmaceutically acceptable solvent, suspending agent or vehicle for delivering a compound of the present invention to the animal or human. The carrier may be liquid or solid and is selected with the planned manner of administration in mind. A "pharmaceutically acceptable" component is one that is suitable for use with humans and/or animals without undue adverse side effects (such as toxicity, irritation, and allergic response) commensurate with a reasonable benefit/risk ratio.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (eg., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein. Techniques and compositions for making dosage forms useful in the present invention are described in the following references: 7 Modem Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound that enhances absorption or penetration of the active ingredient through the skin or other affected areas. Examples of such dermal penetration enhancers include dimethylsulfoxide and related analogues.

The oil phase of an emulsion used to treat subjects in the present invention may be constituted from ingredients known to one of skill in the art in light of the present disclosure. An emulsion may comprise one or more emulsifiers. For example, an oily phase may comprise at least one emulsifier with a fat or an oil, with both a fat and an oil, or a hydrophilic emulsifier may be included together with a lipophilic emulsifier that acts as a stabilizer. Together, the emulsifier(s), with or without stabilizer(s), make up an emulsifying wax, and the wax together with the oil and/or fat make up the emulsifying ointment base that forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono- or dibasic alkyl esters, mineral oil. The choice of suitable oils or fats for the formulation is based on achieving the desired cosmetic properties, the properties required and compatibility with the active ingredient.

Compounds of the present invention may also be administered vaginally, for example, as pessaries, tampons, creams, gels, pastes, foams or spray formulations containing appropriate carriers in addition to the active ingredient. Such carriers are known in the art in light of the present disclosure.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

In general, water, a suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol. Suitable pharmaceutical carriers are described in Remington, cited supra.

The present invention additionally contemplates administering compounds of the herein described invention for use in the form of veterinary formulations, which may be prepared, for example, by methods that are conventional in the art in light of the present disclosure.

Useful pharmaceutical dosage formulations for administration of the compounds of the present invention are illustrated as follows:

Capsules: A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets: A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 ml contains 100 mg of finely divided active ingredient, 200 mg of sodium carboxymethyl cellulose, 5 mg of sodium benzoate, 1.0 g of sorbitol solution, U.S.P., and 0.025 ml of vanillin.

Compounds of the present invention may be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

H. Method of Treatment

The method of treatment can be any suitable method which is effective in the treatment of the particular cancer or viral infection that is being treated. Treatment includes administering a therapeutically effective amount of the compounds of the present invention in a form described hereinabove, to a subject in need of treatment.

Compounds of the present invention can be administered by any means that produces contact of the active agent with the agent's site of action in the body, for example, suitable means including, but not limited to, oral, rectal, nasal, topical (including transdermal, aerosol, buccal or sublingual), vaginal, parenteral (including subcutaneous, intramuscular, intravenous or intradermal), intravesical, or injection into or around the cancer or site of viral infection. They can be administered by any conventional means available for use in conjunction with pharmaceuticals, either as individual therapeutic agents or in a combination of therapeutics. Preferably, compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder, or in a liquid form, or as a liposome.

The preferred route will vary with the condition and age of the recipient, virus or cancer being treated nature of the disorder, or severity of disorder. It is believed that oral administration, or parenteral treatment is the preferred method of administering the compounds to subjects in need thereof.

In each of the above-described methods, the administering may be in vivo, or may be ex vivo. In vivo treatment is useful for treating diseases in a mammal, preferably the mammal is a human; and ex vivo treatment is useful for purging body fluids, such as blood, plasma, bone marrow, and the like, for return to the body. The nation's blood supply is currently tested for antibodies to HIV. However, the test is still imperfect and samples that yield negative tests can still contain HIV virus. Treating blood and blood products with the compounds of the present invention can add an extra margin of safety to kill any retrovirus that may have gone undetected. Body tissue may be internal or external to an animal body, or, for example, may be the surface skin of the animal.

I. Combination Therapy

Compounds of the present invention may additionally be combined with chemotherapeutic agents and/or potentiators to provide a combination therapy. Combination therapy is intended to include any chemically compatible combination of a compound of the present invention with other compounds of the present invention or other compounds outside of the present invention, as long as the combination does not eliminate the activity of the compound of the present invention. For example, one or more compounds may be combined with a potentiator or with a chemotherapeutic agent. In the case of retroviral infection, a combination therapy with nucleoside analogues such as AZT, nonnucleoside reverse transcriptase inhibitors, TC-3, or protease inhibitors is contemplated by the present invention. In the case of hepatitis, acyclovir, famciclovir or valacyclovir, Ribavirin, interferon, or combinations of Ribavirin and interferon or beta globulin is contemplated as a combination therapy. For herpes, a recombinant alpha interferon can be used as a combination therapy. The active agent can be coadministered, for example, in the form of a tablet or capsule, liposome, as an agglomerated powder, or in a liquid form. The amount of chemotherapeutic agent or potentiator used can be lower than that of the benzimidazole derivative. It will be present in a dosage unit in an amount that provides an operative combination with the benzimidazole derivative. The dosage of the chemotherapeutic agent or the potentiator can range from about 0.5 mg/kg body weight to about 400 mg/kg body weight.

Combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example, treatment with one agent on day 1 and the other on day 2. The exact regimen will depend on the disorder being treated, the severity of the disorder, and the response to the treatment.

In addition to the use of chemotherapeutic agents and potentiators, a benzimidazole derivate or a salt or a prodrug thereof can be combined with a fungicide or an herbicide. Preferred herbicides and fungicides include carbendazim, fluoconazole, benomyl, glyphosate, and propicodazole.

J. Pharmaceutical Kits

The present invention also includes pharmaceutical kits useful, for example, for the treatment of cancer or viral infection. The kits comprise one or more containers containing a pharmaceutical composition comprising a therapeutically effective amount of a compound of the present invention. Such kits can further include, if desired, one or more of various conventional pharmaceutical kit components, such as, for example, containers with one or more pharmaceutically acceptable carriers, additional containers, etc., as will be readily apparent to those skilled in the art. Instruction, such as printed instructions for example, either as inserts or as labels, the instruction indicating quantities of the components to be administered, guidelines for administration, and/or guidelines for mixing the components, can also be included in the kit.

K. Studies

The following studies were performed to test the effectiveness of the benzimidazole derivatives of the present invention against certain cancers and viral infections.

Colon and Melanoma Tumor Cells Test:

The following cell culture tests were performed to test the toxicity of benzimidazole derivative compounds of the present invention on colon and melanoma tumor cells. The viability of the cells were tested by looking at MTT (3-[4,5-dimethylthiazol-2-yl]-2,5-diphenyltetrazolium bromide) reduction. MTT assay is a well known measure of cell viability.

The colon tumor cells (HT29) and the melanoma cells (B16 murine melanoma) were seeded (1000–2000 cells) into each well of a 96-well microtiter plate and allowed to grow. Twenty-four hours later, increasing concentrations of each benzimidazole derivative were added to the plates and the cells were allowed to incubate for 3–6 days in the presence of the drugs. MTT reagent was then added to the wells and allowed to incubate for 4 hours at 37° C., after which the formazan metabolite was solubilized with acidic isopropanol and the absorbance was read. Experimental controls included blank wells to which no cells were added (zero point of formazan absorbance) and control wells to which no drug was added (highest level of formazan absorbance). Each drug concentration was tested in duplicate and the resulting average absorbance was plotted against drug concentration using the EZ-ED50 computer program on a personal computer interfaced to the microtiter plate reader. The program fit the resulting curves to a four-parameter equation:

$$Y = \frac{A_{max} - A_{min}}{\left(1 + \frac{X}{IC50}\right)^n} + A_{min}$$

where $A_{max}$ and $A_{min}$ are, respectively, the absorbances in the absence and presence of highest drug concentration, X is the drug concentration and Y is the absorbance at that concentration, n is the slope of the curve, and $IC_{50}$ is the concentration of drug that gives 50% growth inhibition. The $IC_{50}$ value is then derived from this equation by EZ-ED50. The $IC_{50}$ values for growth inhibition of both B16 and HT29 cancer cell lines are reported in Table 4 below (Y=H unless otherwise indicated).

TABLE 4

MTT Assay - Growth Inhibitory Activity

| Cpd. No. | $IC_{50}$ ($\mu$M) | |
|---|---|---|
| | Murine Melanoma | Human Colon Carcinoma |
| 1-1 | 14.8 | 23.6 |
| 1-2 | 29.5 | 38.4 |
| 1-3 | 8.9 | 27.1 |
| 1-4 | 73.5 | 66.0 |
| 1-5 | 32.5 | 52.0 |
| 1-6 | 33.9 | 31.9 |
| 1-7 | 115.6 | 80.6 |
| 2-1 | 181.9 | 252.8 |
| 2-2 | 1.7 | 2.0 |
| 2-3 | 14.2 | 11.1 |
| 2-4 | 200.6 | 212.6 |
| 2-5 | 25.6 | 31.3 |
| 2-6 | 292.6 | 374.7 |
| 2-7 | 159.5 | 119.2 |
| 2-8 | 1.8 | 1.9 |
| 2-9 | >100 | >100 |
| 2-10 | 771.5 | 83.8 |
| 2-10* | 112.8 | 91.5 |
| 2-11 | 13.7 | 45.5 |
| 2-12 | 3.1 | 4.1 |

TABLE 4-continued

MTT Assay - Growth Inhibitory Activity

| Cpd. No. | IC$_{50}$ ($\mu$M) | |
|---|---|---|
| | Murine Melanoma | Human Colon Carcinoma |
| 2-12* | 0.98 | 1.9 |
| 2-13* | 0.63 | 0.29 |

*Y = Cl, at the 5(6) position

Microtubule Inhibition Assay:

The benzimidazole derivatives of this invention were evaluated for their ability to inhibit formation of microtubules, following the procedure of Luduena, R. F. and M. C. Roach (*Pharmacol. Ther.* 49: 133–152 (1991)). Tubulin was purified from bovine brain by a cycle of assembly and disassembly, followed by phosphocellulose chromatography and gel filtration (Fellous, A. et al., *Eur. J. Biochem.* 78(1): 167–174 (1977)). The assay was performed by preparing a sample of tubulin protein under conditions which promote polymerization into microtubules (Prasad, V. et al., *J. Protein Chem.* 11(5): 509–515 (1992)), then adding the benzimidazole derivatives, at 2 $\mu$M, and following the time course of polymerization. Microtubule polymerization was followed by performing the reaction in a cuvette and monitoring UV absorbance at 350 nm, allowing direct visualization of the time course of the polymerization. After 30 minutes, polymerization was complete and the percent inhibition of polymerization was calculated as the final absorbance of the reaction taken as a percentage of the final absorbance of a control polymerization reaction run in parallel without drug added. These data are reported in Table 5 below.

TABLE 5

Tubulin Polymerization Inhibition

| Cpd. No. | % Inhibition |
|---|---|
| 1-1 | 25 |
| 1-2 | 28 |
| 1-3 | 20 |
| 1-4 | 63 |
| 1-5 | 38 |
| 1-6 | 31 |
| 1-7 | 15 |
| 2-1 | 17 |
| 2-2 | 3 |
| 2-3 | 19 |
| 2-4 | 10 |
| 2-5 | 31 |
| 2-6 | 0 |
| 2-7 | 21 |
| 2-8 | 15 |
| 2-9 | 18 |
| 2-10 | 36 |
| 2-10* | 23 |
| 2-11 | 48 |
| 2-12 | 0 |
| 2-12* | 22 |
| 2-13* | 50 |

*Y = Cl, at the 5(6) position

DNA Binding Assay:

The DNA binding assay was performed in a manner very similar to that of the MTT cell growth inhibition assay above. The assay was based upon the ability of the test compounds to displace methyl green (Sigma) from DNA and the resultant hydration of the free methyl green molecule to a colorless derivative (Burres, N. S. et al., *J. Nat. Prod.* 55(11): 1582–1587 (1992); Kim and Nordén, *FEDS Lett.* 315(1): 61–64 (1993)). As for the MTT assay, each drug concentration was assayed in duplicate and the data were averaged before analysis. Experimental controls in this assay included wells containing free methyl green solution with no DNA, for fully decolorized background absorbance, and methyl green-DNA complex (Sigma) without drug, for the highest possible methyl green absorbance. Methyl green-DNA in buffer was added to each well to obtain A$_{655}$ of approximately 0.7. Serial dilutions of drug in buffer were added and the plates were mixed, then allowed to stand at room temperature for 24 hours to allow for displacement and hydration of the free methyl green. The absorbance at 655 nm was measured as a function of added drug concentration in an automated microplate reader, and the data were reduced by the computer program EZ-ED50 to derive IC$_{50}$ values (concentration at which 50% of the methyl green is displaced from DNA).

None of the benzimidazole derivatives listed in Table 4 or 5 showed any DNA interaction by this assay.

EXAMPLES

Example 1

Synthesis of Cpd. No. 1-4

0.200 Gram (1.5 mmol) of 2-aminobenzimidazole was dissolved in 4 mL dry pyridine and one equivalent (1.5 mmol, 200 mg) of benzyl isocyanate was added under argon. The mixture was stirred for 16 hours under argon at 23° C. and another equivalent of benzyl isocyanate was then added. After four more hours stirring under argon at 23° C., the mixture was poured into 20 mL water to precipitate the product. The product was collected by filtration, washed with water and dried under reduced pressure for 16 hours to provide 0.234 g (0.879 mmol, 58.6% yield) of white powder.

Example 2

Synthesis of Cpd. No. 1-5

0.200 Gram (1.5 mmol) of 2-aminobenzimidazole was dissolved in 4 mL dry pyridine and one equivalent (1.5 mmol, 256 mg) of benzyl chloroformate was added under argon. The mixture was stirred for 16 hours under argon at 23° C. and another equivalent of benzyl chloroformate was then added. After four more hours stirring under argon at 23° C., the mixture was poured into 20 mL water to precipitate the product. The product was collected by filtration, washed with water and dried under reduced pressure for 16 hours to provide 0.168 g (0.629 mol, 41.9% yield) of white powder.

Example 3

Synthesis of Cpd. No. 2-11

0.112 Gram (0.421 mmol) of Cpd. No. 1-4, from Example 1, was dissolved in 1 mL dry pyridine and heated to 80° C. for 5 hours with stirring. Six mL water was added to the mixture with stirring and the solid precipitate was collected by filtration, washed with water, and dried under reduced pressure for 16 hours. 0.074 g (0.277 mmol, 65.8% yield) of off-white powdery product was obtained.

Example 4

Synthesis of Cpd. No. 2-9

0.040 Gram (0.150 mmol) of Cpd. No. 1-5, from Example 2, was dissolved in 4 mL toluene and heated to 110° C. with stirring for 24 hours. The mixture was cooled in an ice-water bath and the precipitated solid collected by filtration to provide 0.024 g (0.090 mmol, 60% yield) of product as a white powder.

Example 5

Synthesis of Cpd. No. 2-7

Gram (0.131 mmol) of methyl 2-aminobenzimidazole carbamate was mixed with 2 mL of toluene and 0.696 g (6.55 mmol) of diethylene glycol. Three mg of aluminum isopropoxide was added and the mixture was heated to 110° C. for 15 hours. The toluene was evaporated under a stream of argon with continued heating, then the heat was removed and the residue was treated with 4 mL of boiling water. The resulting mixture was cooled to 23° C., then stored 18 hours at 4° C. The precipitate that formed was collected by filtration and dried under reduced pressure to provide 0.029 g (0.109 mmol, 83.2% yield) of product as off-white flakes.

Example 6

Synthesis of Cpd. No. 2-5

0.025 Gram (0.131 mmol) of methyl 2-aminobenzimidazole carbamate was mixed with 2 mL of toluene and 0.817 g (6.55 mmol) of 2-(2-chloroethoxy) ethanol. Three mg of aluminum isopropoxide was added and the mixture was heated to 110° C. for 15 hours. The toluene was evaporated under a stream of argon with continued heating, then the heat was removed and the residue was treated with 4 ml of boiling water. The resulting mixture was cooled to 23° C., then stored 18 hours at 4° C. The precipitate that formed was collected by filtration and dried under reduced pressure to provide 0.026 g (0.09 mmol, 68.7% yield) of product as off-white powder.

Example 7

Synthesis of Cpd. No. 2-4

0.025 g (0.131 mmol) of methyl 2-aminobenzimidazole carbamate was mixed with 2 ml of toluene and 0.689 g (6.55 mmol) of 2-(2-aminoethoxy)ethanol. Three mg of aluminum isopropoxide was added and the mixture was heated to 110° C. for 15 hours. The toluene was evaporated under a stream of argon with continued heating, then the heat was removed and the residue was treated with 4 ml of boiling water. The resulting mixture was cooled to 23° C., then stored 18 hours at 4° C. The precipitate that formed was collected by filtration and dried under reduced pressure to provide 0.009 g (0.034 mmol, 25.9% yield) of product as colorless plate-like crystals.

What is claimed is:

1. A compound having the following formula A-3:

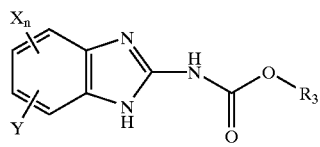

A-3 wherein,
$R_3$ is hydroxyalkyl, hydroxyalkoxyalkyl, or hydroxypoly(alkoxy)alkyl;
when X is hydrogen, alkyl, alkenyl, cycloalkyl, haloalkyl, haloalkenyl, bromo, chloro, fluoro, nitro, at amino; and Y is alkyl, alkenyl, cycloalkyl, haloalkyl, haloalkenyl, bromo, chloro, fluoro, nitro, or amino; or
$R_3$ is hydroxyalkoxyalkyl, or hydroxypoly(alkoxy)alkyl; when each of X and Y is hydrogen; and
n is 1, 2, or 3.

2. The compound of claim 1 wherein X and Y are hydrogen.

3. The compound of claim 2 wherein $R_3$ is hydroxypoly(alkoxy)alkyl.

4. The compound of claim 2 wherein $R_3$ is hydroxyalkoxyalkyl.

5. The compound of claim 1 wherein X is hydrogen, and Y is chloro and is in the 5(6) position.

6. A pharmaceutically acceptable salt of a compound having the following A-3:

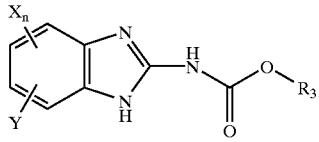

A-3 wherein,
$R_3$ is hydroxyalkyl, hydroxyalkoxyalkyl, or hydroxypoly(alkoxy)alkyl;
each of X mad Y is independently hydrogen, alkyl, alkenyl, cycloalkyl, haloalkyl, haloalkenyl, bromo, chloro, fluoro, nitro, or amino; and
n is 1, 2, or 3.

7. The pharmaceutically acceptable salt of claim 6 wherein said salt is selected from the group consisting of chloride, bromide, sulfate, nitrate, phosphate, sulfonate, formate, tartrate, maleate, malate, citrate, benzoate, salicylate, ascorbate and mixtures thereof.

8. The pharmaceutically acceptable salt of claim 6 wherein said salt is a hydrochloride salt.

9. A prodrug of a compound having the following formula A-3:

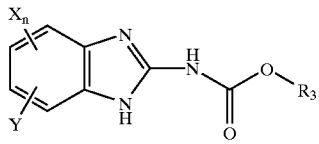

A-3 wherein,
$R_3$ is haloalkyl, alkenyl, haloalkenyl, cycloalkyl, cycloalkalkyl, heterocycloalkyl, heterocycloalkyl, substituted or unsubstituted benzyl, hydroxyalkyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;
when X is hydrogen, alkyl, alkenyl, cycloalkyl, haloalkyl, haloalkenyl, bromo, chloro, fluoro, nitro, or amino; and Y is alkyl, alkenyl, cycloalkyl, haloalkyl, haloalkenyl, bromo, chloro, fluoro, or amino; or
$R_3$ is haloalkenyl, cycloalkyl, cycloalkaalkyl, heterocycloalkyl, heterocycloalkalkyl, unsubstituted benzyl, hydroxyalkyl, hydroxyalkoxyalkyl, hydroxypoly(alkoxy)alkyl, haloalkoxyalkyl, halopoly(alkoxy)alkyl, or aminoalkyl;

when each of X and Y is hydrogen; and n is 1, 2, or 3.

10. A pharmaceutical composition comprising a therapeutically effective amount of a compound of the following formula:

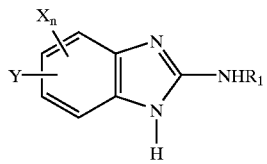

wherein,

R$_1$ is —COOR$_3$;

R$_3$ is hydroxyalkoxyalkyl, or hydroxypoly(alkoxy)alkyl;

each of X and Y is independently hydrogen, alkyl, alkenyl, cycloalkyl, haloalkyl, haloalkenyl, halogen, nitro, or amino; and n is 1, 2, or 3;

and, a pharmaceutically acceptable carrier.

11. A pharmaceutically composition comprising a therapeutically effective amount of a compound of the following formula:

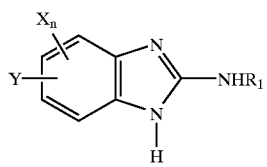

wherein,

R$_1$ is —COOR$_3$;

R$_3$ is haloalkyl, alkenyl, haloalkenyl, cycloalkyl, cycloalkalkyl, heterocycloalkyl, heterocycloalkyl, substituted or unsubstituted benzyl, hydroxyalkyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;

each of X and Y is independently hydrogen, alkyl, alkenyl, cycloalkyl, haloalkyl, haloalkenyl, halogen, nitro, or amino; and n is 1, 2, or 3;

and, a pharmaceutically acceptable carrier wherein the carrier is in the form of a liposome delivery system.

12. A pharmaceutically composition comprising a therapeutically effective amount of a compound of the following formula:

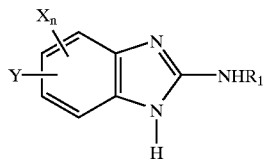

wherein,

R$_1$ is —COOR$_3$;

R$_3$ is hydroxyalkyl, hydroxyalkoxyalkyl, hydroxypoly(alkoxy)alkyl;

each of X and Y is independently hydrogen, alkyl, alkenyl, cycloalkyl, haloalkyl, haloalkenyl, halogen, nitro, or amino; and n is 1, 2, or 3;

and, a pharmaceutically acceptable carrier wherein said compound is micronized and said composition is suitable for administration by injection.

13. A pharmaceutical composition comprising a therapeutically effective amount of a compound of the following formula:

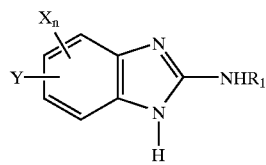

wherein,

R$_1$ is —COOR$_3$;

R$_3$ is haloalkyl, alkenyl, haloalkenyl, cycloalkyl, cycloalkalkyl, heterocycloalkyl, heterocycloalkyl, substituted or unsubstituted benzyl, hydroxyalkyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;

each of X and Y is independently hydrogen, alkyl, alkenyl, cycloalkyl, haloalkyl, haloalkenyl, halogen, nitro, or amino; and n is 1, 2, or 3;

and, a pharmaceutically acceptable carrier wherein said carrier is a soluble polymer and the compound is coupled to the soluble polymer.

14. A pharmaceutical composition comprising a therapeutically effective amount of a compound of the following formula:

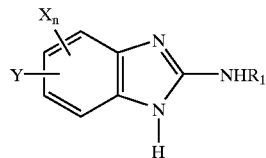

wherein,

R$_1$ is —COOR$_3$;

R$_3$ is haloalkyl, alkenyl, haloalkenyl, cycloalkyl, cycloalkalkyl, heterocycloalkyl, heterocycloalkyl, substituted or unsubstituted benzyl, hydroxyalkyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;

each of X and Y is independently hydrogen, alkyl, alkenyl, cycloalkyl, haloalkyl, haloalkenyl, halogen, nitro, or amino; and n is 1, 2, or 3;

and, a pharmaceutically acceptable carrier wherein said carrier is a biodegradable polymer and the compound is coupled to the biodegradable polymer.

15. The composition of claim 10 in the form of a unit dosage comprising from 1 mg to 1000 mg of said compound.

16. A pharmaceutical composition comprising a therapeutically effective amount of a compound of the following formula A-3:

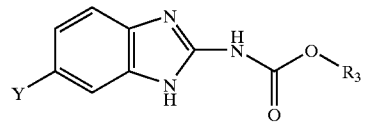

A-3 wherein $R_3$ is hydroxyalkoxyalkyl, or hydroxypoly(alkoxy)alkyl; and Y is hydrogen or chloro.

* * * * *

UNITED STATES PATENT AND TRADEMARK OFFICE
CERTIFICATE OF CORRECTION

PATENT NO. : 6,720,349 B2
DATED : April 13, 2004
INVENTOR(S) : James C. Quada, Jr., et al.

It is certified that error appears in the above-identified patent and that said Letters Patent is hereby corrected as shown below:

Column 28,
Line 1, delete "at" and replace with -- or --;
Line 16, insert -- formula -- immediately after "following";
Line 29, delete "mad" and replace with -- and --;
Line 53, delete the second occurrence of "heterocycloalkyl" and replace with -- heterocycloalkalkyl --;
Line 61, insert -- nitro -- immediately after "fluoro,";
Line 63, delete "cycloalkaalkyl" and replace with -- cycloalkalkyl --.

Column 29,
Line 24, delete "pharmaceutically" and replace with -- pharmaceutical --;
Line 40, delete the second occurrence of "heterocycloalkyl" and replace with -- heterocycloalkalkyl --;
Line 52, delete "pharmaceutically" and replace with -- pharmaceutical --;

Column 30,
Line 27, delete the second occurrence of "heterocycloalkyl" and replace with -- heterocycloalkalkyl --;
Line 59, delete the second occurrence of "heterocycloalkyl" and replace with -- heterocycloalkalkyl --.

Signed and Sealed this

Fifteenth Day of February, 2005

JON W. DUDAS
*Director of the United States Patent and Trademark Office*